US007144736B2

(12) United States Patent
Noda et al.

(10) Patent No.: US 7,144,736 B2
(45) Date of Patent: Dec. 5, 2006

(54) METHOD AND APPARATUS FOR CONTINUOUS FRACTIONAL ANALYSIS OF METALLIC MERCURY AND WATER-SOLUBLE MERCURY IN A GAS

(75) Inventors: Naoki Noda, Kanagawa (JP); Shigeo Ito, Kanagawa (JP); Koji Marumoto, Tokyo (JP); Koji Tanida, Osaka (JP); Munehiro Hoshino, Osaka (JP)

(73) Assignees: Central Research Institute of Electric Power Industry, Tokyo (JP); Nippon Instruments Corporation, Tokyo (JP)

( * ) Notice: Subject to any disclaimer, the term of this patent is extended or adjusted under 35 U.S.C. 154(b) by 677 days.

(21) Appl. No.: 10/363,807

(22) PCT Filed: Jun. 25, 2001

(86) PCT No.: PCT/JP01/05388

§ 371 (c)(1),
(2), (4) Date: Mar. 6, 2003

(87) PCT Pub. No.: WO02/21122

PCT Pub. Date: Mar. 14, 2002

(65) Prior Publication Data

US 2003/0180187 A1    Sep. 25, 2003

(51) Int. Cl.
G01N 33/20 (2006.01)
G01N 21/33 (2006.01)
G01N 21/01 (2006.01)
G01N 1/22 (2006.01)

(52) U.S. Cl. ............ 436/81; 422/50; 422/62; 422/83; 422/88; 422/91; 422/93; 436/73; 436/171; 436/172; 436/177; 436/178; 436/181; 436/182

(58) Field of Classification Search ............ None
See application file for complete search history.

(56) References Cited

U.S. PATENT DOCUMENTS 2,345,090 A * 3/1944 Porter .................. 436/81

(Continued)

FOREIGN PATENT DOCUMENTS

JP     57-17857    * 1/1982

(Continued)

OTHER PUBLICATIONS

Goto, M. et al, Analytica Chimica Acta 1982, 140, 179-185.*
Brindle, I. D. et al, Spectrochimica Acta Part B 1996, 51, 1777-1780.*

(Continued)

*Primary Examiner*—Arlen Soderquist
(74) *Attorney, Agent, or Firm*—Notaro & Michalos P.C.

(57) ABSTRACT

A method and an apparatus which continuously separate and measure mercury in an exhaust gas in accordance with each chemical conformation and display a measurement result in real time. According to the method and the apparatus, water-soluble mercury in a gas is absorbed into an absorption solution (7), the gas and the absorption solution (7) are then separated from each other, the water-soluble mercury in the absorption solution (7) is reduced to be converted into gaseous metal mercury and led to an analyzer (20), and metal mercury in the gas which is not absorbed into the absorption solution (7) is led to an analyzer (22) in the form of gas. As a result, the water-soluble mercury and the non-water-soluble mercury contained in the gas can be captured and measured/analyzed in respective measurement systems in accordance with each chemical conformation. In addition, a concentration of the metal mercury and that of the water-soluble mercury in the gas can be continuously monitored in real time. In this analysis, it is preferable to use the absorption solution (7) to absorb an acid gas which is an inhibitive component to mercury measurement, together with the water-soluble mercury.

4 Claims, 3 Drawing Sheets

U.S. PATENT DOCUMENTS

| | | | | |
|---|---|---|---|---|
| 3,641,821 A | * | 2/1972 | Neuberger et al. | 436/181 |
| 3,713,776 A | * | 1/1973 | Capuano | 422/62 |
| 3,826,618 A | * | 7/1974 | Capuano | 436/43 |
| 3,844,719 A | * | 10/1974 | Hammitt | 422/82.09 |
| 3,933,431 A | * | 1/1976 | Trujillo et al. | 436/76 |
| 4,758,519 A | * | 7/1988 | Nakao et al. | 436/81 |
| 5,277,056 A | * | 1/1994 | Braun et al. | 73/23.31 |
| 5,487,871 A | * | 1/1996 | McDow et al. | 422/80 |
| 5,597,535 A | * | 1/1997 | Schaedlich et al. | 422/88 |
| 5,679,957 A | * | 10/1997 | Durham et al. | 250/373 |
| 5,879,948 A | * | 3/1999 | Van Pelt et al. | 436/81 |
| 6,475,802 B1 | * | 11/2002 | Schaedlich et al. | 436/81 |

FOREIGN PATENT DOCUMENTS

| | | | |
|---|---|---|---|
| JP | 58-19250 | * | 2/1983 |
| JP | 58-196443 | * | 11/1983 |
| JP | 63-191059 | * | 8/1988 |
| JP | 6-241990 | * | 9/1994 |

OTHER PUBLICATIONS

A State-of-the-Art Review of Flue Gas Mercury Spe . . . (EPRI TR-107080 3471 Final Report Nov. 1996).

Examination about Contiuous Analysis . . . (The 8th Symposium Lecture Papers p. 279-282, Kyoto Univ.).

* cited by examiner (Prior Art)

METHOD AND APPARATUS FOR CONTINUOUS FRACTIONAL ANALYSIS OF METALLIC MERCURY AND WATER-SOLUBLE MERCURY IN A GAS

TECHNICAL FIELD

The present invention relates to a method and an apparatus for fractionating mercury in a gas in accordance with chemical conformations, namely, into metal mercury and water-soluble mercury and continuously analyzing them. More particularly, the present invention relates to an improvement in continuous concentration analysis suitable for chemical conformation-based analysis of mercury contained in a gas exhausted from various kinds of plants, e.g., a fossil fuel combustion facility, a waste incineration facility, or a chemical process.

TECHNICAL TERM

A term "water-soluble mercury" used in this specification means free ions or mercury ions in a compound conformation.

BACKGROUND ART

In recent years, in advance of suppression of emission of harmful air pollutants, mercury in an exhaust gas is a substance of a greatest concern. In particular, in movement of enshrining PRTR (Pollutant Release and Transfer Register) into law, it can be considered that monitoring heavy metals emitted from a waste incineration facility and the like will become an important problem in the future, and interests in mercury in an exhaust gas are increasing. Since mercury in a gas such as an exhaust gas containing various kinds of reactive substances changes its chemical conformation and its behavior greatly varies, it is considered that measurement in accordance with each conformation is necessary in regard to clarification of actual conditions and an extraction ratio. Further, in order to comprehend fluctuations in a short time and comprehend specification of a material concerning chemical reaction with the mercury or the influence by a combustion condition, analysis in accordance with each chemical conformation of the mercury must be rapidly carried out.

On the other hand, as a conventional method of measuring mercury in an exhaust gas, a method for measuring all of mercury by using a potassium permanganate solution specified by Japan Industrial Standards (JIS K-0222), a method for measuring metal mercury by using gold amalgam, and others are standard.

Furthermore, there is proposed in Japanese utility model publication No. 19250/1983 a technique of fractionating and measuring molecular mercury consisting of a mercury compound and metal mercury consisting of mercury atoms when such both types of mercury exist in a gas. As shown in FIG. 3, according to this technique, a molecular mercury capturing portion 101 obtained by filling powder of a heat-resisting porous material such as diatomaceous earth in a quartz tube including an electric wire heater 102 on an outer side thereof and a metal mercury capturing portion 107 obtained by filling in a quartz tube including an electric wire heater 108 on an outer side thereof a material obtained by coating the surface of powder of a heat-resisting porous material such as diatomaceous earth with gold are arranged in series, a spectral line absorption cell 110 and an exhaust tube 117 are connected to an outlet of the metal mercury capturing portion 107 through a three-way change-over valve 109, and they are connected to a pump 112 through a filter 111. Moreover, the pump 112 is connected to a flow meter 116 through a branch tube including needle valves 113 and 114 and a three-way change-over valve, an exhaust flow quantity is measured, and then a gas is exhausted.

According to this apparatus, a gas 100 containing mercury led from a sample intake tube 104 by operating the three-way change-over valve 103 is passed through the molecular mercury capturing portion 101 and the metal mercury capturing portion 107, and then exhausted through the pump 112, the branch tube having the needle valve 113 and the flow meter 116 from the exhaust tube 117 without passing through the cell 110. Then, the molecular mercury is absorbed into and captured by the porous material of the molecular mercury capturing portion 101, and the metal mercury which is hardly absorbed by the porous material is captured by forming the amalgam between the metal mercury and gold surface of the porous material. Thereafter, air purified by a filter 106 and a dehumidifier 105 is passed through the molecular mercury capturing portion 101, the metal mercury capturing portion 107 and others and the remaining sample gas is exhausted by switching the three-way change-over valve 103 and connecting the branch tube including the needle valve 114 to the flow meter 116. After scavenging, the amalgam is decomposed by heating the metal mercury capturing portion 107 to approximately 600° C., the metal mercury is disengaged to be led to the cell 110 together with a carrier gas, and the metal mercury is detected by atomic absorption analysis. Subsequently, the molecular mercury in a compound absorbed in the porous material is disengaged by heating the molecular mercury capturing portion 101 to approximately 600° C., it is supplied to the metal mercury capturing portion 107 together with the carrier gas, it is completely decomposed in the metal mercury capturing portion 107 to be turned into metal mercury, and then it is led into the cell 110, thereby detecting the metal mercury by atomic absorption analysis. In this manner, the molecular mercury and the metal mercury can be separately measured.

In addition, in recent years, analysis based on each chemical conformation is attempted also in the United States. This analysis based on each chemical conformation is batch processing carried out by causing the water-soluble mercury to be absorbed by potassium chloride in the former stage, causing the metal mercury to be absorbed by a potassium permanganate solution in the latter stage and measuring a quantity of mercury contained in each solution.

Additionally, an analysis method using a potassium permanganate solution which is specified by Japan Industrial Standards is a batch processing technique, and its target is restricted to monitoring a concentration of all of mercury including all conformations. Therefore, it is impossible to obtain a result of continuous analysis based on each chemical conformation, e.g., fractionation and analysis of the water-soluble mercury and the metal mercury. Further, since the measuring method using gold amalgam aims at only the metal mercury, a result of continuous analysis based on each chemical conformation can not be obtained.

Furthermore, since the fractional detection apparatus for the molecular mercury and the metal mercury disclosed in Japanese utility model publication No. 19250/1983 corresponds to batch processing by which the molecular mercury and the metal mercury are captured by causing them to be absorbed into the porous material or forming the amalgam, scavenging is carried out, the metal mercury capturing portion 107 is first heated to approximately 600° C. and the molecular mercury is disengaged and measured and the molecular mercury capturing portion 101 is then heated to approximately 600° C. to disengage and measure the molecular mercury, sampling is time-consuming, and time is also required for processing before and after sampling, heating carried out for two times and sample analysis. Also, rapid analysis based on each chemical conformation is hardly carried out, and there is a problem of requiring a large amount of cost.

Therefore, it is difficult to comprehend fluctuations in mercury contained in a waste combustion exhaust gas in a short time by any analysis method.

Thus, it is an object of the present invention to provide a method and an apparatus for continuously fractionating and analyzing metal mercury and water-soluble mercury, which continuously separate and measure the mercury in an exhaust gas in accordance with each chemical conformation to display the result in real time.

DISCLOSURE OF INVENTION

To achieve this aim, in a method for continuously fractionating and analyzing metal mercury and water-soluble mercury in a gas according to the present invention, a gas containing mercury is brought into contact with a solution which absorbs water-soluble metal, the water-soluble mercury in the gas is absorbed into the solution, the solution and the gas are separated from each other, and then the metal mercury remaining in the gaseous form in the gas is measured. On the other hand, the water-soluble mercury (mercury ion) absorbed into the solution is reduced, converted into the gaseous metal mercury, shifted to a gas phase and then measured.

In addition, an apparatus for continuously fractionating and analyzing metal mercury and water-soluble mercury according to the present invention comprises: a first reactor which leads and brings a gas containing mercury into contact with a solution which absorbs the water-soluble mercury, and causes the water-soluble mercury in the gas to be absorbed into the solution; a first gas-liquid separator which separates the gas and the solution from each other after gas-liquid contact; a first mercury detection portion which measures the gaseous metal mercury in the gas separated by the gas-liquid separator; a second reaction tube which brings the solution having absorbed the water-soluble mercury into contact with a reduction solution, mixes it with air or an inert gas, reduces the water-soluble mercury in the solution, and shifts it to a gas phase as the gaseous metal mercury; a second gas-liquid separation tube which separates the reduction solution and the gas containing the gaseous metal mercury from each other; and a second mercury detection portion which measures the water-soluble mercury shifted into the gas separated through the second gas-liquid separation tube, thereby fractionating the mercury in the gas into the metal mercury and the water-soluble mercury in accordance with each chemical conformation and continuously measuring them.

Therefore, in the continuous fractional analysis method and the continuous fractional analysis apparatus according to the present invention, the water-soluble mercury is removed from the gas by causing the water-soluble mercury in the gas to be absorbed into the solution, the gaseous metal mercury remaining in the gas without being absorbed into the solution is led to the first mercury detection portion and analyzed. On the other hand, the water-soluble mercury absorbed into the solution is mixed with the reduction solution and reduced, shifted to a gas phase, converted into a gaseous metal mercury, and led to the second mercury detection portion where it is analyzed. As a result, the mercury contained in the gas is fractionated in accordance with the respective chemical conformations, i.e., the water-soluble mercury and the metal mercury, and they are simultaneously measured/analyzed. Additionally, a total quantity of mercury in the gas is calculated by adding a measured quantity of the metal mercury and that of the water-soluble mercury which are separately measured. Thus, the mercury included in the gas can be continuously fractionated to the respective chemical conformations, i.e., the water-soluble mercury and the metal mercury and they can be simultaneously measured/analyzed. That is, according to the continuous fractional analysis method and apparatus of the present invention, concentrations of the metal mercury and the water-soluble mercury in the gas can be continuously monitored in real time. Further, since the metal mercury and the water-soluble mercury are separately measured, a total quantity of mercury can be calculated by adding their measured quantities.

In one embodiment of the continuous analysis method according to the present invention, an acid gas which is a component inhibiting measurement of the mercury is absorbed together with the water-soluble mercury by the absorption solution. In this case, since the acid gas included in the gas can be an obstacle when measuring the metal mercury, a stable result of measurement/analysis can be readily obtained by causing it to be absorbed by water or an alkaline solution together with the water-soluble mercury. That is, since the acid gas which is a component of inhibiting measurement of mercury is absorbed together with the water-soluble mercury by the absorption solution, the acid gas which can be an obstacle when measuring the metal mercury can be absorbed in advance, and a stable result of measurement/analysis can be readily obtained. Furthermore, since the mercury measurement inhibiting substance can be removed simultaneously with removal of the water-soluble mercury from gas by absorption, an additional facility does not have to be provided, thereby resulting in a reduced facility cost.

Moreover, in another embodiment of the continuous analysis method according to the present invention, continuous fractional analysis of the metal mercury and the water-soluble mercury is automatically and continuously carried out, and fractionation, measurement and concentration display are realized in real time simultaneously with sampling. In this case, fractionation, measurement and concentration measurement can be performed simultaneously with sampling and real-time display of results of the measurement is realized by continuously effecting contact of the water-soluble mercury with the absorption solution, separation of the absorption solution and the gas from each other, reduction of the mercury in the absorption solution and separation of the generated gas, dehumidification of the gas, and movement of the gas into the measuring device.

BEST MODE FOR CARRYING OUT THE INVENTION

Figure 1:
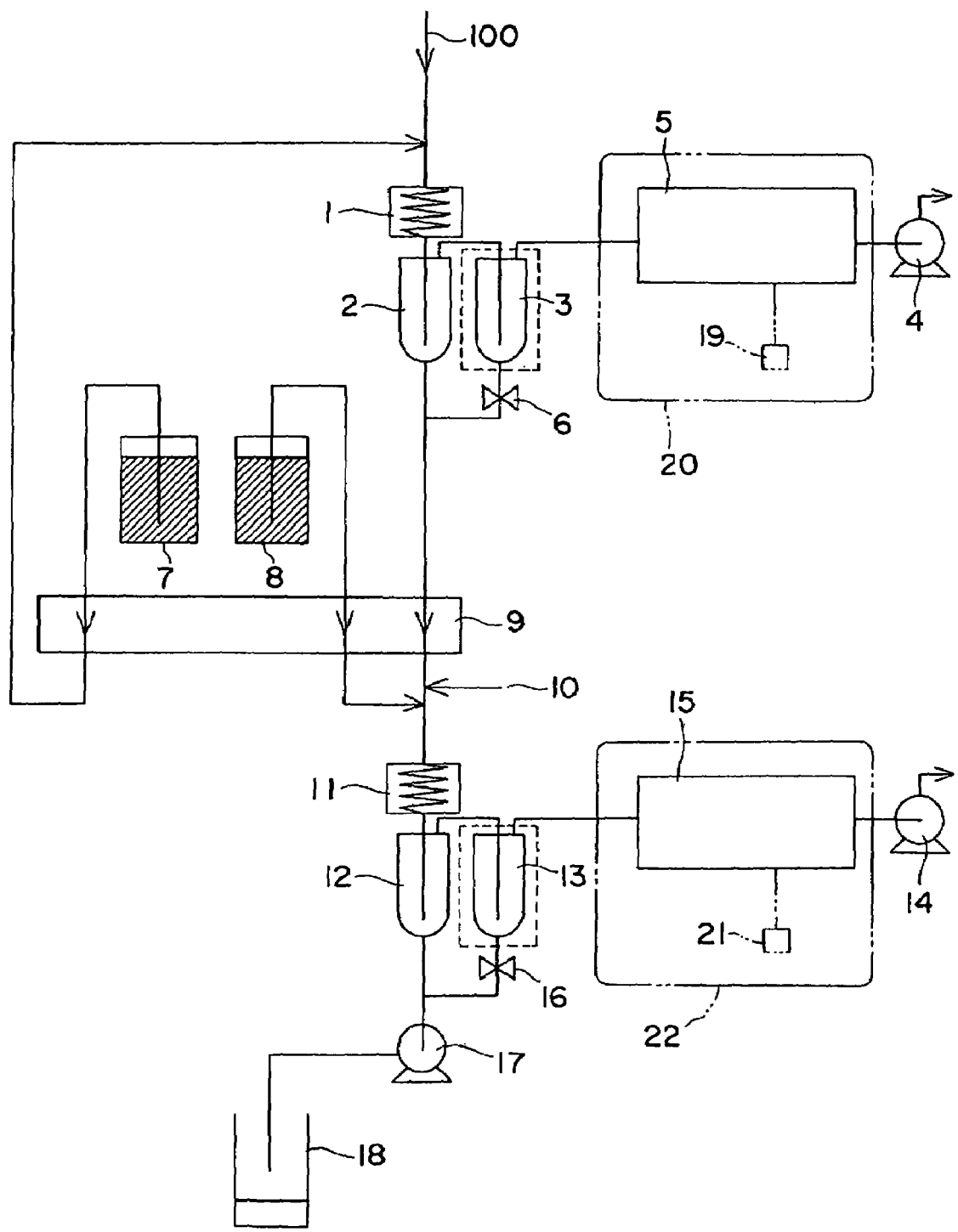
FIG. 1 is a schematic type drawing of a mercury analyzer showing a first embodiment according to the present invention.

A structure of the present invention will now be described in detail based on the best mode illustrated in the drawings.

FIG. 1 shows an embodiment of an apparatus which carries out a method for continuously fractionating and analyzing metal mercury and water-soluble mercury in a gas according to the present invention. This analysis apparatus includes: a first reactor 1 which brings a gas 100 containing mercury into contact with a solution (which will be referred to as an absorption solution hereinafter) 7 which absorbs water-soluble mercury and causes the water-soluble mercury in the gas to be absorbed into the absorption solution; a first gas-liquid separator 2 which separates a gas and the absorption solution 7 after the gas-liquid contact and takes out a gaseous metal mercury which has not been absorbed by the absorption solution 7; a first mercury detection portion 5 which measures the gaseous metal mercury remaining in the gas which has been separated by the gas-liquid separator 2; a second reaction tube 11 which brings the absorption solution 7 which has absorbed the water-solution mercury into contact with a reduction solution 8, mixes it with air (or an inert gas) 10, reduces the water-soluble mercury in the absorption solution 7, and shifts it to a gas phase as gaseous metal mercury; a second gas-liquid separation tube 12 which separates a gas containing the gaseous metal mercury from the absorption solution 7 after the reduction; and a second mercury detection portion 15 which measures the water-soluble mercury shifted into the gas which has been separated through the second gas-liquid separation tube 12, thereby fractionating the mercury in the gas into the metal mercury and the water-soluble mercury in accordance with each chemical conformation and continuously measuring them.

The first mercury detection portion 5 constitutes a first analyzer 20 together with a terminal 19 such as a personal computer connected thereto. The second mercury detection portion 15 constitutes the second analyzer 22 together with a terminal 21 connected thereto. The first analyzer 20 and the second analyzer 22 are devices capable of performing automatic and continuous analysis. Furthermore, data collection can be automated by using collecting devices such as personal computers as the terminals 19 and 21. Although not shown, each of the analyzers 20 and 22 includes a flow meter used to measure concentrations of the metal mercury and the water-soluble mercury in the gas or a concentration of all of mercury.

Here, the first reactor 1 consists of a reaction tube which causes gas-liquid contact of the absorption solution and the gas 100. Furthermore, the metal mercury which is not absorbed into the absorption solution 7 remains in the gas and is separated from the absorption solution 7 by the first gas-liquid separator 2, and moisture is removed from the gas by a first dehumidification tube 3. Then, the metal mercury is induced by a first air pump 4 and led to the first mercury detection portion 5.

On the other hand, the second reactor 11 consists of a reaction tube which effects mixing/gas-liquid contact of the solution 7 which has absorbed the water-soluble mercury taken out from the first gas-liquid separator 2 and the first dehumidification tube 3, air 10 and a reduction solution 8, and causes a reduction reaction. Moreover, the water-soluble mercury absorbed into the absorption solution is reduced, gasified and shifted to a gas phase (air 10), it is separated from the reduction solution by the second gas-liquid separator 12, and moisture is removed from the gas by the second dehumidification tube 13. Then, the water-soluble mercury is induced by a second air pump 14 and led to a second mercury detection portion 15. In addition, the absorption solution which has completed reduction reaction is taken out by a drainage pump 17 and discharged into a drain tank 18.

It is to be noted that a drain valve 6 is periodically opened and the moisture colleted by the first dehumidification tube 3 is led into the second reactor 11 by a pump 9. A drain valve 16 is periodically opened and the moisture collected by the second dehumidification tube 13 is taken out by a drainage pump 17 and discharged into a drain tank 18.

The absorption solution 7 and the reduction solution 8 are reserved in respective reservoir tanks, and a necessary quantity is supplied from each tank by a solution pump (peristaltic pump) 9. The absorption solution 7 is a solution capable of absorbing the water-soluble mercury, and use of a solution suitable for absorption of mercury, e.g., water, salts such as a potassium chloride solution (KCl solution), alkalis such as a sodium hydroxide solution (NaOH solution) or a potassium hydroxide solution (KOH solution), or acid such as a nitric acid solution ($HNO_3$) is preferable. Among them, although water or an alkali solution is preferable since it can simultaneously absorb the water-soluble mercury and acid in a contact sample, the present invention is not restricted thereto. In the case of using acid for the absorption solution 7, cleansing tubes using an alkali solution are added to the latter stages of the dehumidification tubes 3 and 13, thereby removing an inhibitive component to mercury measurement. In addition, as the reduction solution 8, use of a solution suitable for reducing the water-soluble mercury, for example, tin chloride (II) dihydrate ($SnCl_2/2H_2O$), sodium borohydride ($NaBH_4$) or a slannous oxide solution is preferable. However, the absorption solution 7 or the reduction solution 8 is not restricted to those exemplified above, and any material can be used as long as it can absorb or reduce the water-soluble mercury.

Incidentally, in the mercury continuous fractional analysis apparatus according to this embodiment, the gas including the metal mercury is removed from the first gas-liquid separator 2 by the first air pump 4, the gas including the metal mercury obtained by reducing the water-soluble mercury in the absorption solution 7 is removed from the second gas-liquid separator 12 by the second air pump 14, and the air 10 is blown into the absorption solution 7 including the water-soluble mercury or the absorption solution 7 having the reduction solution 8 mixed therein by using the second air pump 14, all of which is carried out by utilizing induced draft.

Continuous fractional analysis of mercury using the mercury analyzer according to this embodiment will now be described.

The exhaust gas 100 is first sucked by the first air pump 4, mixed with the absorption solution 7 such as water, salts, an alkali or an acid in the first reactor 1 and subjected to gas-liquid contact. Here, the divalent water-soluble mercury and the divalent water-soluble organic mercury in the gas are moved into the absorption solution 7, and the gas and the absorption solution 7 are separated from each other in the first gas-liquid separation tube 2. On the other hand, since the gaseous metal mercury does not dissolve in the absorption solution 7 but exists in the gas, the gaseous metal mercury is led into the first mercury detection portion 5 through the first dehumidification tube 3, and it is measured/analyzed by the first analyzer 20 based on the principle of the atomic absorption method or the like.

Incidentally, when bringing the exhaust gas into gas-liquid contact with the absorption solution 7 in the first reactor 1, it is preferable to absorb the acid gas included in the exhaust gas together with the water-soluble mercury. In this case, the acid gas which can be an inhibitive component to mercury measurement can be removed in advance, thereby readily obtaining a stable result of measurement/analysis.

Furthermore, the absorption solution 7 separated in the first gas-liquid separation tube 2 is supplied to the second reactor 11 by the solution pump 9 while containing the water-soluble mercury, and it is mixed with the reduction solution 8 at a position before the second reactor 11. This mixed solution is brought into gas-liquid contact with air sucked by the second air pump 14 in the second reactor 11, reduces the water-soluble mercury to the gaseous metal mercury and shifts it to a gas phase. Subsequently, the gas and the absorption solution 7 are separated from each other in the second gas-liquid separator 12, the gaseous metal mercury is led into the second mercury detection portion 15 through the second dehumidification tube 13, and it is measured/analyzed in the second analyzer 22 in the manner similar to the above.

As described above, according to the mercury detector of this embodiment, the metal mercury which is not absorbed into the absorption solution 7 is detected by the mercury detection portion on the first stage, and the water-soluble mercury absorbed into the absorption solution 7 is reduced to be the detectable gaseous metal mercury and then detected by the mercury detection portion on the latter stage. That is, the water-soluble mercury and the metal mercury in the gas can be continuously fractionated, and individually and simultaneously analyzed. Therefore, simultaneous measurement of a content of each mercury in the gas enables the gaseous metal mercury and the water-soluble mercury in the exhaust gas to be continuously fractionated and measured in real time. Further, a mercury concentration based on each chemical conformation and a concentration of all kinds of mercury can be obtained.

Furthermore, the continuous fractional analysis method according to this embodiment is useful for continuous monitoring of concentrations of the water-soluble mercury and the metal mercury in the gas and particularly for detection of a concentration of mercury in a waste incineration exhaust gas. Moreover, useful data regarding exhaust can be obtained in the study of mercury in the air environment. In addition, it is preferable to carry out the present invention in continuous monitoring of gaseous mercury in any other process gas based on each chemical conformation as well as a waste incineration exhaust gas.

Figure 2:
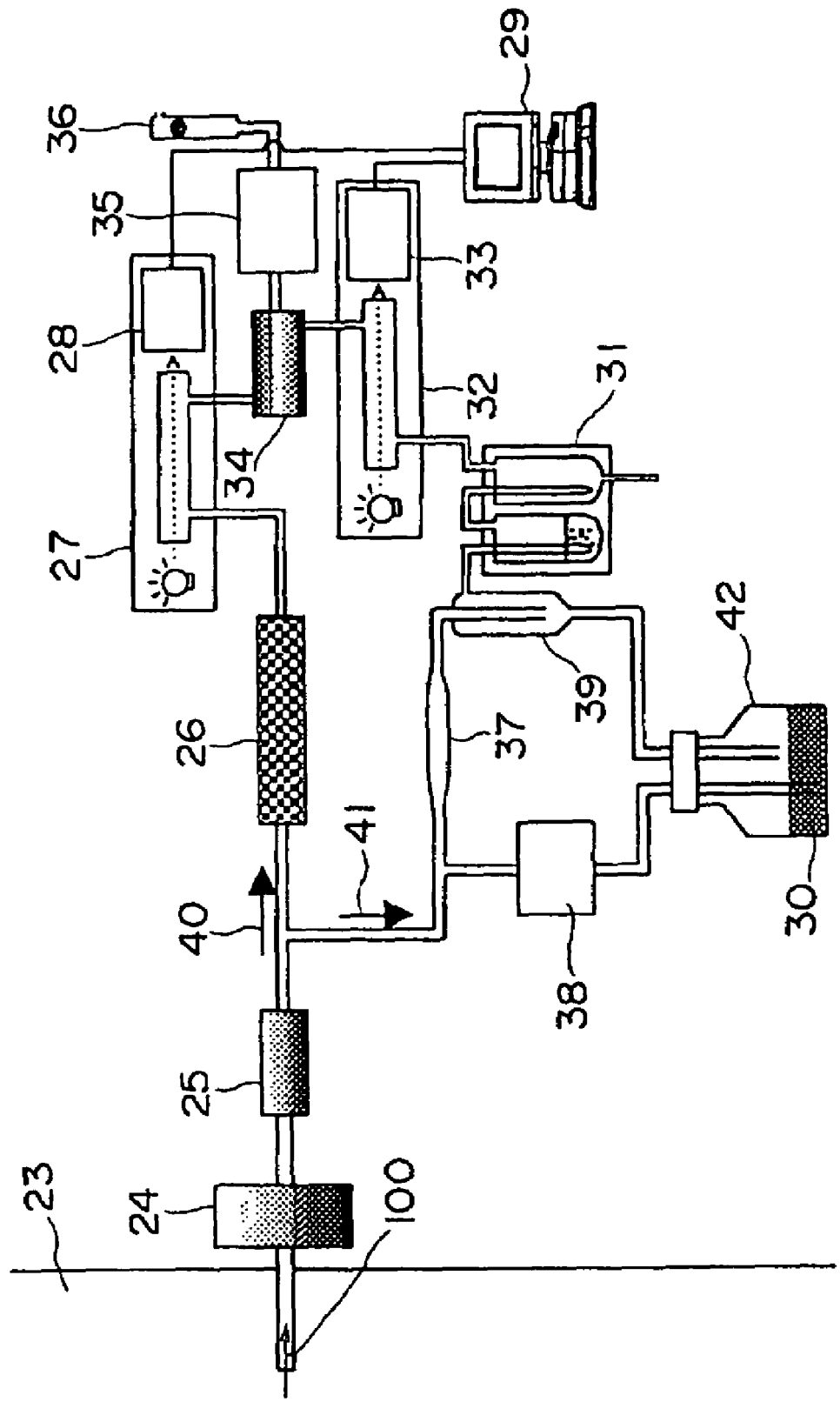
FIG. 2 is a schematic type drawing of a mercury analyzer showing a second embodiment according to the present invention.
Figure 3:
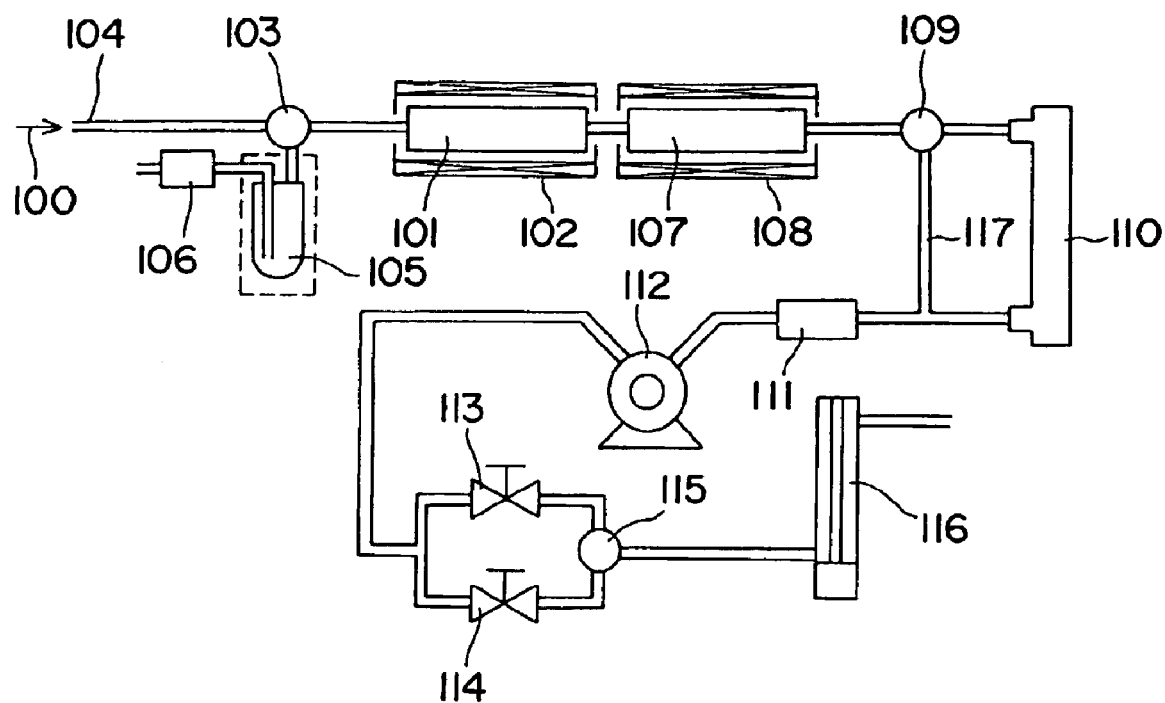
FIG. 3 is a schematic type drawing of a conventional mercury analyzer based on each chemical conformation.

FIG. 2 shows another embodiment. A continuous fractional analysis system according to this embodiment realizes the parallel processing of detection of metal mercury and detection of water-soluble mercury. A gas containing mercury, e.g., a flue gas 100 is extracted from a flue 23 in which the flue gas 100 flows through a filter 24 and a dehumidification tube 25. A part of this gas is supplied to a first mercury detection portion 27 through a first path 40, and another part of the same is supplied to a second mercury detection portion 32 through a second path 41, thereby detecting metal mercury in the gas. It is to be noted that the filter 24 and the dehumidification tube 25 remove dusts and moisture in the gas as pre-processing.

The first path 40 is used to analyze gaseous metal mercury Hg(0) contained in the flue gas 100, and it first removes an acid gas such as NOx, SOx or HCl contained in the exhaust gas by an acid gas removal device 26 and then leads the remaining gas to a mercury detection portion 27 where Hg(0) is detected and analyzed. Analysis of mercury in the mercury detection portion 27 is quantitative determination analysis based on the atomic absorption analysis using, e.g., a detector 28 and a terminal 29 such as a personal computer. It is to be noted that an instantaneous detection quantity of mercury is obtained by using a detected curve and integrating detection is obtained by integration of the curve according to the atomic absorption analysis.

The second path 41 mixes a reducing agent 30 consisting of $SnCl_2$ or $NaBH_4$ with the flue gas 100 to cause active gas-liquid contact in a reaction tube 37 so that all of mercury compounds existing in the exhaust gas is gasified by reduction. As a result, all of mercury including the original gaseous metal mercury and the water-soluble mercury which has been reduced to be the metal mercury exists in the gas separated from a reduction solution 30 in a gas-liquid separator 39 in the form of the detectable gaseous metal mercury. Thus, a gas which has passed through a cooler box 31 consisting of an acid gas removal tube and a dehumidification tube and from which the acid gas and the moisture are removed is led to a mercury detection portion 32 including a detector 33 where all of mercury is detected and whose quantity is determined. It is to be noted that the reference numeral 38 in the drawing designates a pump which sucks the reducing agent 30 accommodated in a container 42, supplies it to the second path 41 and mixes the reducing agent 30 with the exhaust gas led to the second path 42.

Here, since a quantity of the metal mercury is detected/measured in the first path 40 and a quantity of all mercury is detected/measured in the second path 41, divalent mercury ion Hg(II), namely, the water-soluble mercury is calculated from a difference of these measured values. In addition, the gas whose quantity has been determined in the mercury detection portion 27 and the mercury detection portion 32 is led by an air pump 35, passes through activated carbon 34 and a flow meter 36 and then is emitted.

It is to be noted that the foregoing embodiments are examples of the preferred embodiments according to the present invention, but the present invention is not restricted thereto and various modifications can be carried out without departing from the scope of the invention.

The invention claimed is:

1. A method for continuously fractionating and analyzing metal mercury and water-soluble mercury in a gas, comprising steps of:
   bringing a gas containing mercury into contact with a solution which absorbs water-soluble metal to cause water-soluble mercury in the gas to be absorbed into the solution;
   separating the solution and the gas from each other to measure metal mercury remaining in a gaseous form in the gas;
   reducing the water-soluble mercury absorbed into the solution to convert the water-soluble mercury into gaseous metal mercury; and
   shifting the gaseous metal mercury to a gas phase to be measured.

2. The method for continuously fractionating and analyzing metal mercury and water-soluble mercury in a gas according to claim 1, wherein the solution is used to absorb an acid gas which is an inhibitive component to mercury measurement, with the water-soluble mercury.

3. The method for continuously fractionating and analyzing metal mercury and water-soluble mercury in a gas according to claim 1 or claim 2, wherein continuous fractional analysis of the metal mercury and the water-soluble mercury is automatically and continuously performed, and fractionation, measurement and concentration display are carried out in real time simultaneously with sampling.

4. An apparatus for continuously fractionating and analyzing metal mercury and water-soluble mercury in a gas, the apparatus fractionating mercury in a gas into metal mercury and water-soluble mercury in accordance with each chemical conformation and continuously measuring them, comprising:

a first reactor for leading a gas containing mercury, bringing it into contact with a solution which absorbs water-soluble mercury, and causing the water-soluble mercury in the gas to be absorbed into the solution;

a first gas-liquid separator for separating the gas and the solution from each other after the gas-liquid contact;

a first mercury detection portion for measuring gaseous metal mercury in the gas separated by the gas-liquid separator;

a second reaction tube for bringing the solution which has absorbed the water-soluble mercury into contact with a reduction solution, mixing it with air or an inert gas, reducing the water-soluble mercury in the solution to be gaseous metal mercury, and shifting the gaseous metal mercury to a gas phase;

a second gas-liquid separation tube for separating the reduction solution and a gas containing the gaseous metal mercury from each other; and a second mercury detection portion for measuring the water-soluble mercury shifted into the gas separated through the second gas-liquid separation tube.

* * * * *